United States Patent [19]

Appelgren et al.

[11] Patent Number: 4,840,799

[45] Date of Patent: Jun. 20, 1989

[54] PROCESS FOR PREPARING RAPIDLY DISINTEGRATING GRANULATES

[75] Inventors: Curt H. Appelgren, Kungsbacka; Eva C. Eskilsson, Mölnlycke; Jonas P. Uvdal, Gothenburg, all of Sweden

[73] Assignee: Lejus Medical Aktiebolag, Molndal, Sweden

[21] Appl. No.: 15,011

[22] Filed: Feb. 17, 1987

[30] Foreign Application Priority Data

Feb. 14, 1986 [SE] Sweden ................................. 8600657

[51] Int. Cl.$^4$ ............................................. A61K 9/50
[52] U.S. Cl. ...................... 424/493; 424/489; 424/490; 424/494; 424/495; 424/497; 424/498
[58] Field of Search ............... 424/489, 499, 500, 501, 424/502, 494, 490, 495, 497, 498, 493

[56] References Cited

U.S. PATENT DOCUMENTS

| | | | |
|---|---|---|---|
| 4,456,628 | 6/1984 | Bauer et al. | 424/494 X |
| 4,525,339 | 6/1985 | Behl et al. | 424/494 X |
| 4,533,562 | 8/1985 | Ikegami et al. | 427/3 |
| 4,673,564 | 6/1987 | Kawata et al. | 424/494 |

FOREIGN PATENT DOCUMENTS

| | | | |
|---|---|---|---|
| 45-005277 | 2/1971 | Japan | 424/494 |
| 58-077811 | 5/1983 | Japan | 424/494 |

*Primary Examiner*—Thurman K. Page
*Attorney, Agent, or Firm*—Burns, Doane, Swecker & Mathis

[57] ABSTRACT

The present invention relates to a process for preparing a rapidly disintegrating core granulate containing a pharmaceutically active compound, which granulate is optionally intended to be coated with a release determining coating, as well as such cores, whereby one adds a pharmaceutically active compound, optionally together with an emulsifier, to a solvent, and optionally treats the composition obtained intensively, optionally while reducing its particle size, distributes the treated composition obtained over a bed of a solid, preferably water soluble material, and dries the agglomerates thus obtained to the so as to form a rapidly disintegrating core granulate.

20 Claims, No Drawings

PROCESS FOR PREPARING RAPIDLY DISINTEGRATING GRANULATES

DESCRIPTION

1. Technical Field

The present invention relates to a rapidly disintegrating and in relation to the pure, untreated pharmaceutically active compound present therein, a rapidly releasing core granulate, and a process for its preparation.

The object of the present invention is primarily to obtain a composition, which gives a high bioavailability and the desired plasma concentration-time profile with regard to substantially hardly soluble therapeutically active compounds by creating the composition as a rapidly disintegrating, rapidly releasing core granulate, whereby the disintegration of the granulate with reference to place and time can be regulated in a simple way by means of a release controlling protecting coating.

A further object is to obtain a rapidly disintegrating core, the disintegration of which with regard to place and rate per se is controlled by a protective coating controlling the place and time.

2. The Background of the Invention

It is well known that bioavailability particularly of slightly soluble active compounds is highly dependent on the particle size of the active compound-or its specific surface area. The greater the area of the particle the greater the solubility rate in gastrointestinal juice prior to absorption through the mucous membranes.

It is, however, also known that bioavailability can not always be improved as desired, only by preparing the compound in a very fine particulate form (micronizing). These difficulties are particularly pronounced when the substance in spite of a small particle size is released during a long time period and over a long distance in the gastrointestinal tract.

There is also a problem using compounds having a medium solubility, and which are absorbed over a very small part of the intestine-they show a so called absorption window. The compounds having a medium solubility can show a diminished bioavailability. It is particularly important that the compound is released in the right place and in a complete way during a time period being acceptably brief.

The demands on modern pharmaceuticals are thus great, preferably with the intention of reaching a maximal therapeutic effect using a minimum amount of compound in order thereby to reduce the frequency of and the degree of side effects, as well as inter- and intra individual variations.

In order to obtain this, a process step is required that gives an increased rate to complete dissolution of the compound, which dissolution can be controlled to take place in any desired place in the gastrointestinal tract. This dissolution must thereby be carried out in such a way that precipitation and recrystallization of the compound is avoided.

DESCRIPTION OF THE PRESENT INVENTION

It has now surprisingly been shown possible to be able to solve the above given problems and to obtain a rapidly disintegrating core granulate, wherein a pharmaceutically active compound shows a high availability, whereby the invention is characterized in that a particulate, relatively slightly soluble compound has been provided with a layer of an emulsifier/tenside having the same HLB-value as the solubility of the active compound, or has formed a true emulsion using such an emulsifier/tenside, in the presence of a solvent and has been applied onto a solid material so as to form an agglomerate, whereupon drying is carried out to form a granulate.

The invention includes a process for preparing rapidly disintegrating core granulates, as well, which granulates are preferably intended to be provided with a release controlling coating, whereby the process is characterized in that one provides a slightly soluble, pharmaceutically active compound with one or more emulsifiers/tensides, which have an HLB-value corresponding to that of the solubility of the slightly soluble compound, and a solvent, or a mixture of solvents to obtain a pumpable composition, which is subject to an intense treatment, whereupon the thus obtained, treated composition is administered over a bed of one or more solid materials functioning as a carrying surface having a large effective surface area, which material has nonbinding properties to said active compound, which material is preferably water soluble, whereby an agglomerate is obtained which is dried to a granulate of irregular, or, preferably, spherical form which rapidly disintegrates into primary particles.

A further object of the present invention is to obtain a rapidly disintegrating core, preferably of a given shape. This object is characterized in that a pharmaceutically active compound, together with a water-alkanol mixture having the ratio water:alkanol 40–80:60–20, are added to a bed of solid, watersoluble material comprising microcrystalline cellulose in an amount of <25% by weight, and at least one disintegrating agent in an amount of <25% by weight of the final composition, whereupon the moist bed material is shaped and granulated into spherical cores.

It is possible, in spite of the inclusion of microcrystalline cellulose, which has a binding effect, to obtain a rapid disintegration into primary particles by means of the addition of water:alkanol.

The water is hereby necessary to obtain a formation, while the alkanol has turned out to have a positive impact on the disintegration in spite of the binding effect of the microcrystalline cellulose.

The pharmaceutically active compound can be protected, as is evident from the following discussion, against crystal growth in the dissolution stage by adding, as shown above, an emulsifier.

Further characteristics are evident from the accompanying claims.

By means of the present invention a rapidly disintegrating and releasing granulate or core is obtained, which preferably can be provided with a release controlling coating so that the disintegration and the release take place at the suitable place and with a suitable rate after the administration. It has also turned out that one obtains a higher bioavailability.

Pharmaceutically active compounds which are slightly soluble in water or gastrointestinal juice relates to defined slightly soluble compounds and compounds which have a medium solubility. By the defined slightly soluble compounds, compounds are included which are primarily regarded as having a solubility of <1000 mg/l, and compounds which have a medium solubility, particularly those having an absorption window, are those having a solubility of 1–10 g per liter.

In the former group the following are present, i.e., nifedipine, nimodipine, nivadipine, nitrendipine, nisolidipine, niludipine, nicardipine, felodipine, omeprazole, spironolactone, griseofulvine, furosemide, terbutaline.

In the latter group i.a. such compounds are present as L-dopa, riboflavin, digoxin.

The amount of active compound in the final core is at most 60% by weight, normally, however, preferably 20–30% by weight.

The emulsifier used shall have a HLB-value, i.e., a hydrophilicity-lipophilicity value that substantially corresponds with the solubility properties of the active compound. Emulsifiers that fulfill such conditions are polyoxyethylene sorbitane fatty acid esters (Tween), polyoxystearate, polyethylene glycol. The emulsifier is added in an amount of 5–100% by weight of the active compound, preferably 15–30% by weight, or is about 5% of the final core, but, at most 15–30% by weight of the final core.

In the group of emulsifiers/tensides, wetting agents, such as sodium lauryl sulphate, polyoxy ethylene-polyoxy propylene copolymer (Pluronic), esters of polyhydroxy alcohols, macrogel esters, macrogel ethers, long chain alcohols, macrogel-polyoxy propyl copolymers are present.

Thus one prepares a mixture of active compound, emulsifier/-tenside and a solvent, which can be selected from any suitable organic solvent, or mixture of such, or a mixture with water, or water. If one should wish to have spherical granules, water should preferably be present. The suspension thus obtained is then intensively treated in an intense mixer (homogenizer), dispersing apparatus, or a colloid mill, a pearl mill, pebble mill, or similar equipment for simultaneous micronization, whereby the active compound can dissolve and form a true emulsion together with the emulsifier, be distributed in and covered with emulsifier/tenside, or only become covered with emulsifier. The solubility is dependent on which solvent has been used. The amount of active compound when a true solution is not obtained, controls the viscosity of the suspension obtained, whereby one should always try to get a pumpable suspension. The amount of solvent can be increased, but due to the subsequent steps it is, however, restricted. For this reason the amount of active compound will normally become at most 60% by weight. It is apparent that the amount can be increased when one selects a solvent which dissolves the active compound and a true solution/emulsion is obtained. Suitable solvents are water, methanol, ethanol, isopropanol, t-butanol, acetone, methylethylketone, chlorinated hydrocarbons, aromatic hydrocarbons and others.

The suspension or emulsion obtained is then distributed over a bed of a solid material having a large effective surface area, whereby neither absorption nor adsorption shall take place between the active compound and the bed material. The active compound shall attach without any binding. The bed material consists, preferably of a water soluble material, such as mannitol, lactose, saccharose, glucose, xylitol, sorbitol, phosphates (Na, K), urea, citrates (Na, K), ascorbic acid, fructose. The bed material can also consist of less soluble substances such as starch, Ca-phosphates, and Ca-citrate, or combinations of these two groups. The solid bed is at least 40% by weight, preferably normally 60–90% by weight of the final core.

In order to increase the disintegration rate, the solid bed can include microcrystalline cellulose in an amount of <25% by weight, preferably 2–15% by weight, of the final composition and/or disintegrating agents such as substituted hydroxypropyl cellulose (LHPC), carboxymethyl starch, cross-linked carboxymethyl cellulose, crosslinked starch, or cross-linked polyvinyl pyrrolidone in an amount of <25% by weight, preferably 2–15% by weight of the final composition.

The effective surface area shall be large, which means a particle size of <500 $\mu$m, preferably 50–250 $\mu$m.

The disintegration time for the granulate thus obtained has been determined to be 5–10 min., whereafter primary particles are reobtained.

In order to obtain spherical granules/cores, the moist water containing mass is extruded through an extruder; the extrudate is allowed to pass to a spheronizer, and is dried. To shape spherical granules, microcrystalline cellulose should be included.

By means of this, the thus obtained core, while not controlling the absorption event in the intestine, the coatings are place and rate determining with regard to the release. Thus gastric juice resistent coatings are used, such as shellac, anionic polymer coatings having different $pk_a$-values, mixtures of anionic polymers or anionic polymer(-s) and ethyl cellulose, and Eudragit RS, RL, or more simple non-gastric juice resistant coatings as sugar, water soluble cellulose derivatives and others, if an immediate dissolution in the abdomen is wanted.

The present invention has been tested using nifedipine as a model compound. Cores were prepared having the following composition and in the following way.

EXAMPLE 1

At first a mixture was prepared consisting of nifedipine, active compound: 250 g, solvent: 355 ml, ethanol:-water (40:60), Na-lauryl sulphate: 15 g, Tween 80, emulsifier: 50 g.

The mixture was homogenized in a homogenizer to a slurry and was spread over a bed consisting of:
mannitol: 585 g
microcrystalline cellulose: 50 g
2-hydroxypropyl cellulose: 50 g The moist bed obtained was extruded in an extruder (Nicasystem), was spheronized in a spheronizer (Nicasystem) and dried.

In the corresponding way as in Ex. 1 the following was prepared:

Ex. (2) cores using isopropanol:water (40:60), as solvent;

Ex. (3) cores using the double amount of Na-lauryl sulphate;

Ex. (4) cores without Na-lauryl sulphate;

Ex. (5) cores using water as the only solvent;

Ex. (6) cores using water as the only solvent, but without intense treatment of emulsifier-active compound;

Ex. (7) cores using Na-lauryl sulphate but without emulsifier Tween 80;

Ex. (8) cores using Na-lauryl sulphate, without Tween 80; and without intense treatment Ex. (9) cores with Na-lauryl sulphate, without emulsifier Tween 80, water as the only solvent;

Ex. (10) cores as in (h) but without intense treatment; and

Ex. (11) cores as in Ex. 1, however, without intense treatment.

The release of active compound from the different cores were determined in a standardized test. The results are given in Table 1 below.

TABLE 1.

| Sample | % active compound released after | | |
|---|---|---|---|
| | 1 | 2 | 3 hrs |
| Ex. 1 | 66 | 85 | 94 |
| Ex. 2 | 64 | 83 | 92 |
| Ex. 3 | 52 | 71 | 85 |
| Ex. 4 | 58 | 74 | 85 |
| Ex. 5 | 52 | 68 | 77 |
| Ex. 6 | 10 | 17 | 20 |
| Ex. 7 | 40 | 58 | 65 |
| Ex. 8 | 4 | 8 | 12 |
| Ex. 9 | 6 | 12 | 17 |
| Ex. 10 | 3 | 6 | 7,5 |
| Ex. 11 | 11 | 17 | 23 |

As evident from Table 1 the addition of emulsifier and intense treatment have a determining importance for the release rate, but also the additions of ethanol and isopropanol give an apparent effect.

In another test a core of Ex. 1 above was compared with a core (A), where nifedipine had been micronized together with water, whereupon emulsifier was added and the mixture was granulated with the bed material, i.e., a composition which was the same as that of Ex. 1 with regard to pure composition. The result of the release test is given in Table 2 below.

TABLE 2.

| Sample | % active compound released after | | | | |
|---|---|---|---|---|---|
| | 1 | 2 | 3 | 4 | 6 hrs |
| Ex. 1 | 65 | 85 | 94 | | |
| A | 38 | 51 | 56 | 58 | 66 |

The influence on the release rate of the bed consisting of solid material has also been studied. Cores were prepared in accordance with Ex. 1 using lactose (Ex. 1(l)), maize starch (Ex. 1(ms)), calcium phosphate (Ex. 1(CaP)), and calcium citrate (Ex. 1(CaCi)). The result of the release test is given in Table 3 below.

TABLE 3

| Sample | % active compound released after | | | |
|---|---|---|---|---|
| | 1 | 2 | 3 | 4 hrs |
| Ex. 1 | 65 | 85 | 94 | |
| Ex. 1 (l) | 62 | 76 | 86 | |
| Ex. 1 (ms) | 55 | 63 | 67 | |
| Ex. 1 (CaP) | 35 | 41 | 46 | |
| Ex. 1 (CaCi) | 48 | 61 | 63 | |

Mannitol, lactose, maize starch, and calcium citrate are relatively equal during the first two hours, and then particularly during the first hour, while calcium phosphate is worse. This may depend on the fact that calcium phosphate is not readily dissolved in water, but has a limited solubility.

In a further test, a dried slurry of Ex. 1 above was compared with a dried slurry (NIM) prepared from nifedipine ground with water, and ground to 5-10 μm particle size. The release rate for the ingoing, unground, water slurried, dried nifedipine compound (NIOM), about 50-150 μm particle size was also determined.

The result is evident from Table 4.

TABLE 4

| Sample | % active compound released after | | | | | |
|---|---|---|---|---|---|---|
| | 1 | 2 | 3 | 4 | 5 | 6 hrs |
| Ex. 1 | 63 | 72 | | 85 | | 92 |
| NIM | 22 | 28 | | 37 | | 44 |
| NIOM | 8 | 15 | 17,5 | | | |

As evident from the results of Table 4, a considerably improved release is obtained using a composition prepared in accordance with the present invention. As evident from Table 1 above an improved release is obtained by means of the distribution over and onto the solid material.

We claim:

1. A process for the preparation of a rapidly disintegrating core comprising a pharmaceutically active compound, said process comprising adding an emulsifier/tenside having a HLB-value corresponding to the solubility characteristics of the pharmaceutically active compound in a solution or a suspension of the pharmaceutically active compound in a water:alcohol mixture having a weight ratio of 40-80:60-20 to form a pumpable composition, subjecting the pumpable composition to an intense treatment in an apparatus selected from the group of homogenizer, colloid mill, pearl mill, and pebble mill wherein the composition is distributed over a bed of at least one solid material having a large effective surface area and having nonbinding properties to the said pharmaceutically active compound so as to form an agglomerate, and drying the agglomerate to form a granulate having irregular or spherical form.

2. A process according to claim 1, wherein microcrystalline cellulose is part of the material in said bed and is present in an amount so as to form 2-25% of the granulate.

3. A process according to claim 1, wherein a disintegrating agent is part of the material in said bed and is present in an amount so as to form 2-25% of the granulate.

4. A process according to claim 1, wherein the pharmaceutically active compound has a solubility of less than 1000 mg per liter and is present in an amount of up to 50% of the granulate.

5. A process according to claim 4, wherein the pharmaceutically active compound is selected from the group consisting of nifedipine, nimodipine, nivadipine, nitrendipine, nisoldipine, niludipine, nicardipine, felodipine, omeprazole, spironolactone, griseofulvine, furosemide, and terbutaline.

6. A process according to claim 1, wherein the pharmaceutically active compound has a solubility of 1 to 10 grams per liter, and has an absorption window at the absorption in the gastrointestinal tract.

7. A process according to claim 6, wherein the pharmaceutically active compound is selected from the group consisting of L-dopa, riboflavin, digoxin, and digitoxin.

8. A process according to claim 1, wherein the emulsifier having a corresponding HLB-value is selected from the group consisting of polyoxyethylene sorbitan fatty acid esters, polyoxystearate, and polyethylene glycol, and whereby the emulsifier is added in an amount of 5 to 100% of the weight of the pharmaceutically active compound.

9. A process according to claim 8, wherein the emulsifier is selected from the group consisting of sodium laurylsulphate, polyoxyethylene-polyoxypropylene copolymer, ester of polyhydroxyalcohols, macrogel esters, macrogel ethers, long chain alcohols, and macrogel-polyoxypropylene copolymer.

10. A process according to claim 1, wherein the bed is at least one solid material selected from the group consisting of mannitol, lactose, saccharose, glucose, fructose, sorbitol, xylitol, sodium phosphate, potassium phosphate, urea, citrate, and ascorbic acid wherein said material comprises at least 40% by weight of the granulate.

11. A process according to claim 10, wherein the solid material comprises 60 to 90% by weight of the granulate.

12. A process according to claim 1, wherein the solid material is selected from the group consisting of starch, calcium phosphate, and calcium citrates.

13. A process according to claim 3, wherein the disintegrating agent is selected from the group consisting of substituted hydroxypropylcellulose, carboxymethylstarch, cross-linked carboxymethylcellulose, cross-linked starch, and cross-linked polyvinylpyrrolidone in an amount of 2–15% by weight.

14. A process according to claim 1, wherein the granulate has a disintegration time of 5 to 10 minutes.

15. A process according to claim 1, wherein the solid material in the bed has a particle size of less than 500 microns.

16. A process according to claim 15, wherein said particle size is less than 250 microns.

17. A process according to claim 10, wherein the solid material in the bed has a particle size of less than 500 microns.

18. A process according to claim 11, wherein the solid material in the bed has a particle size of less than 500 microns.

19. A process according to claim 12, wherein the solid material in the bed has a particle size of less than 500 microns.

20. A process according to claim 1, wherein the emulsifier is selected from the group consisting of sodium laurylsulphate, polyoxyethylene-polyoxypropylene copolymer, ester of polyhydroxyalcohols, macrogel esters, macrogel ethers, long chain alcohols, and macrogel-polyoxypropylene copolymer.

* * * * *